United States Patent
Lee et al.

(10) Patent No.: US 8,524,195 B2
(45) Date of Patent: Sep. 3, 2013

(54) IRON OXIDE NANOPARTICLES AS MRI CONTRAST AGENTS AND THEIR PREPARING METHOD

(75) Inventors: Chulhyun Lee, Daejeon (KR); Sung Lan Jeon, Wonju-si (KR); Min Kyung Chae, Seoul (KR); Jee-Hyun Cho, Daejeon (KR); Eun Ju Jang, Daejeon (KR)

(73) Assignee: Korea Basic Science Institute (KR)

( * ) Notice: Subject to any disclaimer, the term of this patent is extended or adjusted under 35 U.S.C. 154(b) by 211 days.

(21) Appl. No.: 12/981,389

(22) Filed: Dec. 29, 2010

(65) Prior Publication Data

US 2011/0165086 A1  Jul. 7, 2011

(30) Foreign Application Priority Data

Jan. 7, 2010  (KR) ........................ 10-2010-0001184

(51) Int. Cl.
*A61B 5/055* (2006.01)
*A61K 51/00* (2006.01)

(52) U.S. Cl.
USPC ........ 424/9.322; 424/1.11; 424/9.3; 424/491; 424/493

(58) Field of Classification Search
USPC ................. 424/1.1, 9, 491, 493, 497, 9.322, 424/173; 428/403, 404
See application file for complete search history.

(56) References Cited

U.S. PATENT DOCUMENTS 4,951,675 A * 8/1990 Groman et al. ............... 424/9.32
2009/0258076 A1* 10/2009 Cheon et al. .................. 424/491

OTHER PUBLICATIONS

Yanglong Hou et al. Controlled synthesis and chemical conversions of FeO nanoparticles, Angew Chem Int Ed 2007, 46, 6329-6332.*

An, Kwangjin, et al., "Synthesis of Uniform Hollow Oxide Nanoparticles through Nanoscale Acid Etching," Nano Letters, vol. 8, No. 12, (2008) 4252-4258.
Cregan, R.F., et al., "Single-Mode Photonic Band Gap Guidance of Light in Air," Science, vol. 285 (Sep. 3, 1999) 1537-1539.
Huang, Jiaxing, et al., "In-Situ Source-Template-Interface Reaction Route to Semiconductor CdS Submicrometer Hollow Spheres," Adv. Mater., vol. 12, No. 11 (2000) 808-811.
Hou, Yanglong, "Controlled Synthesis and Chemical Conversions of FeO Nanoparticles," Angew. Chem. Int. Ed., vol. 46 (2007) 6329-6332.
Im, Sang Hyuk, "Polymer hollow particles with controllable holes in their surfaces," Nature Materials, vol. 4 (Sep. 2005) 671-675.
Liang, Han-Pu, et al. "Pt Hollow Nanospheres: Facile Synthesis and Enhanced Electrocatalysts," Angew. Chem. Int. Ed., vol. 43 (2004) 1540-1543.
Nam, Ki Min, et al., "Single-Crystalline Hollow Face-Centered-Cubic Cobalt Nanoparticles from Solid Face-Centered-Cubic Cobalt Oxide Nanoparticles," Angew. Chem. Int. Ed., vol. 47 (2008) 9504-9508.
Rapoport, L., et al., "Hollow nanoparticles of WS2 as potential solid-state lubricants," Nature, vol. 387 (Jun. 19, 1997) 791-793.
Shin, Jongmin, et al., "Hollow Manganese Oxide Nanoparticles as Multifunctional Agents for Magnetic Resonance Imaging and Drug Delivery," Angew. Chem. Int. Ed., vol. 48 (2009) 321-324.

* cited by examiner

*Primary Examiner* — Michael G Hartley
*Assistant Examiner* — Jagadishwar Samala
(74) *Attorney, Agent, or Firm* — Blakely Sokoloff Taylor & Zafman

(57) ABSTRACT

Iron oxide nano contrast agents for Magnetic Resonance Imaging which have superior $T_2$ contrast effect, and also can be used as a storage or a carrier for drugs and so on, are disclosed. The iron oxide nano contrast agents can be prepared by the steps of: coating surfaces of hydrophobic FeO nanoparticles with a coating material selected from the group consisting of polyethylene glycol-phospholipid conjugate, dextran, chitosan, dimercaptosuccinic acid and mixtures thereof in an organic solvent to form hydrophilic FeO nanoparticles having hydrophilic surfaces and dispersibility in water; dispersing the hydrophilic FeO nanoparticles in water to oxidize FeO; and exposing the oxidized hydrophilic FeO nanoparticles to an acidic buffer to dissolve and remove interior unoxidized FeO portions, and thereby to form $Fe_3O_4$ nanoparticles having an interior space.

7 Claims, 4 Drawing Sheets

IRON OXIDE NANOPARTICLES AS MRI CONTRAST AGENTS AND THEIR PREPARING METHOD

This application claims the priority benefit of Korean Patent Application No. 10-2010-0001184 filed on Jan. 7, 2010. All disclosure of the Korean Patent application is incorporated herein by reference.

FIELD OF THE INVENTION

This invention relates to iron oxide nano contrast agents and a method for preparing the same, and more particularly to novel iron oxide nano contrast agents for Magnetic Resonance Imaging (MRI) which have superior $T_2$ contrast effect for magnetic resonance image, and also can be used as a storage or a carrier for drugs and so on.

BACKGROUNDS OF THE INVENTION

Nanoparticles having hollow or cracked structures are used in various fields such as catalysis, nanoreactor, chemical storage or drug delivery system for drugs, lubrication, nanoelectronics, and so on (Angew. Chem. Int. Ed. 2008, 47, 9504-9508; Angew. Chem. Int. Ed. 2004, 43, 1540-1543; Adv. Mater. 2000, 12, 808-811; Science 1999, 285, 1537-1539, 5; Nature 1997, 387, 791-793; Nat. Mater. 2005, 4, 671-675). Recently, researches for Magnetic Resonance Imaging (MRI) nano contrast agents using the nanoparticles have been actively conducted. MRI contrast agents can be classified into $T_2$ contrast agents using iron oxide nanoparticles and $T_1$ contrast agents using metal oxide of Mn or Gd. The iron oxide nanoparticles, which work as the $T_2$ contrast agents, are conventionally prepared by pyrolysing $FeL_3$ ($L=CO_5$, $NO_3$, acetylacetonate, and so on) precursor to directly obtain $Fe_3O_4$ of uniform sizes. Meanwhile, hollow iron oxide ($Fe_3O_4$) nanoparticles can be prepared by introducing phosphorus into the interior of iron oxide nanoparticles with replacement reaction of phosphoric acid and iron oxide, and then dissolving out the introduced phosphorus (Nano Letters, 2008, 8, 4252-4258). However, the prepared iron oxide nanoparticles include less amount of Fe, and not preferable in $r_2$ value (relaxivity, a value representing contrast effect) and $T_2$ contrast effect, and thus insufficient as MRI $T_2$ contrast agents. In addition, recently, hollow Mn oxide ($Mn_3O_4$) nanoparticles are developed as $T_1$ contrast agents having superior $T_1$ contrast effect. The hollow nanoparticles work not only as MRI contrast agents but also as drug storages or carriers by accommodating drugs in the interior space thereof (Angew. Chem. Int. Ed. 2009, 48, 321-324). However, the $Mn_3O_4$ nanoparticles are prepared with highly toxic Mn, and thus are not preferable for humans' use, and also cannot be used as $T_2$ contrast agents.

SUMMARY OF THE INVENTION

Therefore, it is an object of the present invention to provide iron oxide nano contrast agents which use Fe as a metal having low toxicity and pre-existing in human body.

It is other object of the present invention to provide iron oxide nano contrast agents which have an interior hollow space or crack-shaped grooves, and also include a relatively large amount of Fe.

It is another object of the present invention to provide iron oxide nano contrast agents which have superior MRI $T_2$ contrast effect and can be used as a storage or a carrier for drugs and so on, and a method for preparing the same.

In order to achieve these and other objects, the present invention provides a method for preparing iron oxide nano contrast agents comprising the steps of: coating surfaces of hydrophobic FeO nanoparticles with a coating material selected from the group consisting of polyethylene glycol-phospholipid conjugate, dextran, chitosan, dimercaptosuccinic acid and mixtures thereof in an organic solvent to form hydrophilic FeO nanoparticles having hydrophilic surfaces and dispersibility in water; dispersing the hydrophilic FeO nanoparticles in water to oxidize FeO; and exposing the oxidized hydrophilic FeO nanoparticles to an acidic buffer to dissolve and remove interior unoxidized FeO portions, and thereby to form $Fe_3O_4$ nanoparticles having an interior space.

The present invention also provides hydrophilic FeO nanoparticles which are intermediates for preparing iron oxide nano contrast agents, comprising: hydrophobic FeO nanoparticles; and a coating material which is coated on the surface of the hydrophobic FeO nanoparticles, and selected from the group consisting of polyethylene glycol-phospholipid conjugate, dextran, chitosan, dimercaptosuccinic acid and mixtures thereof, wherein the amount of the coating material is 30 to 200 weight parts with respect to 100 weight parts of the hydrophobic FeO nanoparticles, and the diameter of the hydrophilic FeO nanoparticles is 20 to 100 nm.

The present invention also provides iron oxide nano contrasts agent for magnetic resonance image, comprising: iron oxide ($Fe_3O_4$) nanoparticles having 5 to 50% of interior space with respect to the total volume of the nanoparticles; and a coating material which is coated on the surface of the iron oxide ($Fe_3O_4$) nanoparticles, and selected from the group consisting of polyethylene glycol-phospholipid conjugate, dextran, chitosan, dimercaptosuccinic acid and mixtures thereof, wherein the particle diameter of the iron oxide nano contrast agents is 20 to 100 nm.

The iron oxide nano contrast agents of the present invention have low toxicity to human body because it is prepared with Fe which exists in human body in a relatively large amount. The iron oxide nano contrast agents have relatively high iron content while there is an interior space or crack-shaped grooves in it. Therefore, the iron oxide nano contrast agents have superior MRI $T_2$ contrast effect, and can be used as a storage or carrier for drugs and so on.

DETAILED DESCRIPTION OF THE INVENTION

A more complete appreciation of the invention, and many of the attendant advantages thereof, will be better appreciated with reference to the following detailed description and the accompanying drawings.

Figure 1:
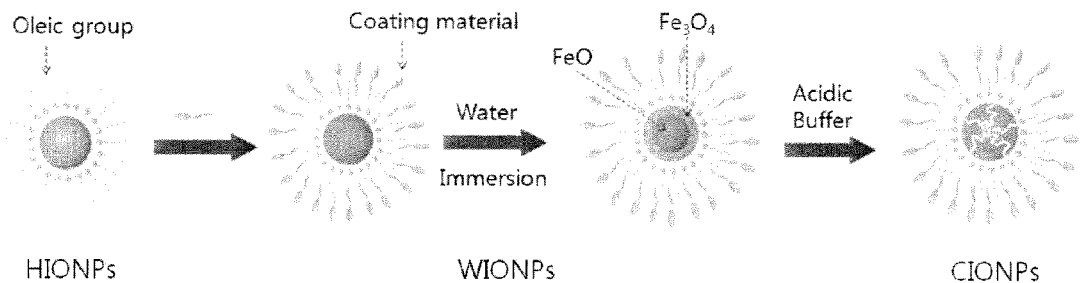
FIG. 1 is a drawing for explaining the method for preparing iron oxide nano contrast agents according to an embodiment of the present invention.

FIG. 1 is a drawing for explaining the method for preparing iron oxide nano contrast agents according to an embodiment of the present invention. As shown in FIG. 1, in order to prepare the nano contrast agents of the present invention, firstly, a coating material selected from the group consisting of polyethylene glycol-phospholipid (PEG-phospholipid) conjugate, dextran, chitosan, dimercaptosuccinic acid (DMSA) and mixtures thereof is coated on the surfaces of hydrophobic FeO nanoparticles (HIONPs) in an organic solvent to form hydrophilic FeO nanoparticles (WIONPs) which have hydrophilic surfaces and can be dispersed (solved) in water. All or most of the FeO nanoparticles are composed of FeO. If necessary, the FeO nanoparticles may contain 0.1 to 10 weight % of $Fe_3O_4$. In this case, the FeO nanoparticles can be expressed as $Fe_xO_y$ nanoparticles which are the mixture of $Fe_3O_4$ and FeO, wherein x is 1 to 3, preferably 1.002 to 1.2, and y is 1 to 4, preferably 1.003 to 1.3.

The organic solvent, in which the hydrophobic FeO nanoparticles (HIONPs) are dispersed, can be a conventional organic solvent such as chloroform ($CHCl_3$), hexane, toluene, dichloromethane, mixtures thereof, and so on. The amount of the organic solvent is 2 to 10 mL, preferably 4 to 8 mL with respect to 10 mg of the hydrophobic FeO nanoparticles. Also, it is preferable to uniformly disperse the hydrophobic FeO nanoparticles by further adding 50 to 200 weight parts of a fatty acid having 15 to 25 carbon atoms, for example, oleic acid with respect to 100 weight parts of the hydrophobic FeO nanoparticles, and thereby increasing the dispersion force of the hydrophobic FeO nanoparticles. The coating material, which is coated on the surface of the hydrophobic FeO nanoparticles, may include both of a hydrophilic part and a hydrophobic part. For example, in the polyethylene glycol-phospholipid conjugate (PEG-pl), the hydrophobic phospholipid part is bonded to the surface of the hydrophobic FeO nanoparticle, if necessary, with an oleic group intervening therebetween, and the polyethylene glycol part works as a hydrophilic part to provide dispersibility in water. Examples of the polyethylene glycol-phospholipid conjugate include DSPE-mPEG 2000 (1,2-distearoyl-sn-glycero-3-phosphoethanolamine-N-methoxy polyethylene glycol, Avanti polar lipid, Inc., $C_{133}H_{267}N_2O_{55}P$, MW=2805.497) of Formula 1, the compound of Formula 2, and so on.

[Formula 1]

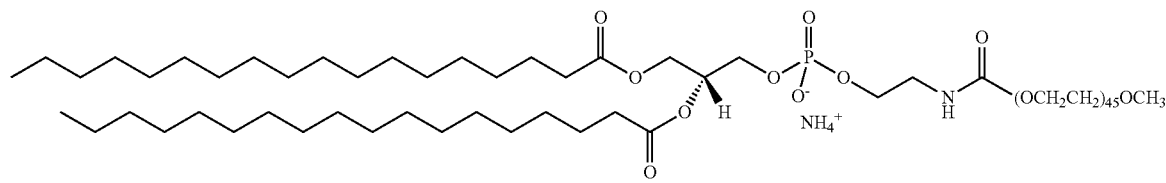

[Formula 2]

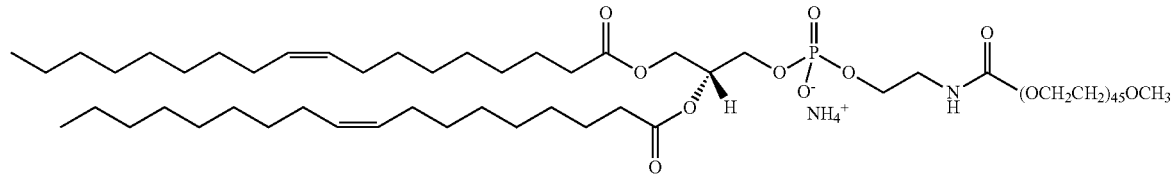

When dimercaptosuccinic acid (DMSA) of Formula 3 is used as the coating material, dimercaptosuccinic acid forms a coating layer on the surface of the hydrophobic FeO nanoparticles through intermolecular disulfide cross-linkages. Therefore, compared with other coating material such as polyethylene glycol-phospholipid conjugate and so on, the dimercaptosuccinic acid can form a thin coating layer, and increase sensitivity to magnetic resonance ($r_2$ value, and so on). In addition, the functional group (carboxylic acid, —COOH) of dimercaptosuccinic acid can be used for introducing a small molecule or an antibody for a cancer targeting.

[Formula 3]

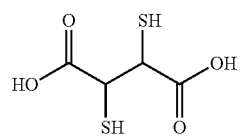

The amount of the coating material is 30 to 200 weight parts, preferably 50 to 150 weight parts, more preferably 80 to 120 weight parts with respect to 100 weight parts of the hydrophobic FeO (iron oxide) nanoparticles (HIONPs). If the amount of the coating material is too little, the dispersibility of the hydrophobic FeO nanoparticles in water may be insufficient because the surfaces of the hydrophobic FeO nanoparticles cannot be fully coated with the coating material. If the amount of the coating material is too much, the excess coating material should be removed by an additional purification step, and there are no additional advantages. Preferably, the reaction time of the hydrophobic FeO nanoparticles (HIONPs) and the coating material in the organic solvent is about 30 minutes to 2 hours. For dimercaptosuccinic acid (DMSA), the preferable reaction time is about 12 to 24 hours. After completion of the reaction, the organic solvent is slowly removed, and the reactants are kept in an oven of reduced pressure and of high temperature for 30 minutes to 2 hours to produce solid phase hydrophilic FeO nanoparticles (WIONPs). The hydrophilic FeO nanoparticles (WIONPs) have a particle diameter of 20 to 100 nm, preferably 30 to 80 nm, and have water dispersibility as hydrophilic particles.

The hydrophobic FeO nanoparticles (HIONPs) can be prepared by various conventional methods. For example, the hydrophobic FeO nanoparticles (HIONPs) can be prepared by oxidizing iron compound (namely, precursor) such as Fe(acetylacetonate)$_3$[iron(III)(acac)$_3$], Fe(NO$_3$)$_3$[iron(III) (nitrate)$_3$], Fe(ClO$_4$)$_3$[iron(III) (perchlorate)$_3$], and mixtures thereof in the presence of solvents and/or surfactants at 250 to 350° C., for example, at high temperature of 300° C. Examples of the solvent and surfactant used in the above reaction include fatty acid having 15 to 25 carbon atoms, more specifically, mixture of oleic acid (OA) and oleylamine (OAm). In this reaction, if alkyl ether, hydrocarbon solvents, or so on having high boiling point of about 250 to 350° C. is used, Fe$_3$O$_4$ is obtained instead of FeO. And, if the oleic acid and the oleylamine are used in the amounts of the same equivalent, hexahedral-shaped nano materials are synthesized, and if oleic acid/oleylamine (OA/OAm) are used by the ratio of 25 mmol/35 mmol, spherical-shaped nano materials are synthesized. Generally, as the amount of oleic acid increases, the size of the produced nanoparticles increases, but the reaction yield decreases. As the amount of the reactant Fe(acac)$_3$ increases, and the reaction temperature and the reaction time increase, the size of the synthesized nanoparticles increases. The hydrophobic FeO nanoparticles prepared by this way have good hydrophobic property due to the oleic groups bonded on their surfaces. Conventionally, the hydrophobic nanoparticles have a particle diameter of 5 to 50 nm, preferably 10 to 30 nm according to reaction conditions (Angew. Chem. Int. Ed. 2007, 46, 6329-6332).

Next, the hydrophilic FeO nanoparticles (WIONPs) is dispersed in water to partially oxidize FeO of the hydrophilic iron oxide (FeO) nanoparticles to Fe$_3$O$_4$ (gray color part in FIG. 1). This step is based on the fact that FeO of the hydrophilic FeO nanoparticles is easily oxidized in water and converted to Fe$_3$O$_4$. The oxidation is slowly carried out from the outer surface to the inner part of the hydrophilic FeO nanoparticles. For example, the oxidation can be carried out until the volume of FeO becomes 10 to 70%, preferably 10 to 50% of total volume of the FeO nanoparticles. In the oxidation step, the amount of the water is generally 5 to 20 mL, preferably 8 to 15 mL with respect to 10 mg of the hydrophilic FeO nanoparticles, and the run-time for the oxidation step is 1 to 50 days, preferably 2 to 40 days. If the run-time for the oxidation step is too long, all FeO of the hydrophilic FeO nanoparticles is oxidized to Fe$_3$O$_4$, and then hollows or cracks may not be formed inside the nanoparticles even though acidic buffer is used in the next step to remove unoxidized parts. If the run-time for the oxidation step is too short, the oxidation is carried out insufficiently. Therefore, when the unoxidized FeO parts are removed by acidic buffer, there is insufficient Fe content in the nanoparticles, and excessive hollows or cracks can be formed in the nanoparticles, and thereby, the nanoparticles may not work as MRI contrast agents.

In the next step, the partially oxidized hydrophilic FeO nanoparticles (WIONPs) are exposed to an acidic buffer, and the unoxidized inner FeO part(s) is dissolved and removed from the nanoparticles to produce Fe$_3$O$_4$ nanoparticles having interior space (CIONPs). All or most of the Fe$_3$O$_4$ nanoparticles (CIONPs) are composed of Fe$_3$O$_4$. However, if necessary, the Fe$_3$O$_4$ nanoparticles (CIONPs) may contain 0.1 to 10 weight % of FeO, and in this case, the Fe$_3$O$_4$ nanoparticles can be expressed as Fe$_x$O$_y$ nanoparticles, which represent a mixture of Fe$_3$O$_4$ and FeO, wherein x is 1 to 3, preferably 2.8 to 2.998, and y is 1 to 4, preferably 3.7 to 3.997. The pH of the acidic buffer is less than pH 7, and the acidity of the acidic buffer solution is maintained during the reaction. The partially oxidized hydrophilic FeO nanoparticles can be exposed to the acidic buffer just after prepared, but preferably can be exposed to the acidic buffer after 1 to 50 days from the preparation date. Examples of the acidic buffer include a phthalate buffer, a citrate buffer, an acetate buffer, mixtures thereof, and so on. The phthalate buffer may include 0.1M of potassium hydrogen phthalate which is mixed with 0.1M NaOH or 0.1M HCl solution to control pH of the buffer. The citrate buffer may include citric acid and sodium citrate, and the acetate buffer may include acetic acid and sodium acetate. The amount of the acidic buffer is preferably 10 to 100 mL with respect to 5 to 30 mg of the partially oxidized hydrophilic FeO nanoparticles. The pH of the acidic buffer solution (reaction solution) is 1 to 6, preferably, 2 to 5, and more preferably 2.3 to 3.5. If the pH of the reaction solution is too low, the nanoparticles (CIONPs) may be decomposed or degenerated, and if the pH of the reaction solution is too high, the inner unoxidized FeO parts may be not sufficiently removed.

The iron oxide (Fe$_3$O$_4$) nanoparticles (CIONPs) of the present invention have one or more interior space, such as an interior hollow space, crack-shaped groove, and so on, and substantially uniform particle sizes. The total volume of the interior space can be varied in wide ranges, but generally is about 5 to 50%, preferably 10 to 30% with respect to the total volume of the Fe$_3$O$_4$ nanoparticles. If the volume of the interior space is too small, the nanoparticles may not be effective as a storage or a carrier for drugs and so on. If the volume of the interior space is too big, the nanoparticles may include less amount of iron, and may not be effective as a MRI contrast agent. Therefore, the iron oxide nano contrast agent, namely, Fe$_3$O$_4$ nanoparticles having interior space (CIONPs) for magnetic resonance image comprises an iron oxide (Fe$_3$O$_4$) nanoparticles having 5 to 50%, preferably 10 to 30% of interior space with respect to the total volume of the iron oxide (Fe$_3$O$_4$) nanoparticles; and a coating material coated on the surface of the iron oxide (Fe$_3$O$_4$) nanoparticles. The particle diameter of the iron oxide nano contrast agent is 20 to 100 nm, preferably 30 to 80 nm. The iron oxide (Fe$_3$O$_4$) nanoparticles of the present invention have similar particle sizes compared with conventional solid Fe$_3$O$_4$ nanoparticles, and slightly low iron concentration, but superior T$_2$ contrast effect. Therefore, the nanoparticles of the present invention are useful as MRI T$_2$ contrast agents, and can be used as a storage or a carrier by accommodating drugs and so on in the inner empty space(s) of the nanoparticles.

Hereinafter, examples and comparative examples are provided to illustrate the present invention in more detail, but the present invention is not restricted or limited by the following examples.

Example 1

Preparation of Iron Oxide Nano Contrast Agent

1. Synthesis of Hydrophobic FeO Nanoparticles (HlONPs)

Fe(acac)$_3$(iron(III)(acetyl acetonate)$_3$, 1.4 g, 4 mmol, precursor), oleic acid (8 mL, 25 mmol) and oleylamine (12 mL, 35 mmol) were added into a 3-neck round-bottom flask, and heated to 120° C. The reactants were stirred under reduced pressure and at the same temperature for 2 hours to remove water and oxygen in the reactants. After 2 hours, the reaction temperature was raised to 220° C. while feeding Ar gas in the reactor. After further reacting for 30 minutes, the reaction temperature was raised to 300° C. (heating rate: 2° C./min). After further reacting for 30 minutes at 300° C., the temperature of the reactor was dropped to room temperature quickly, and excess ethanol was added to the reaction solution. The reactants were centrifuged to obtain precipitated solid (hydrophobic FeO). A small amount of hexane was added to disperse the obtained solid, and excess ethanol was added thereto, and the reactants were centrifuged again to obtain solid product. The obtained solid were dispersed in hexane, and filtrated with syringe filter to obtain hydrophobic FeO nanoparticles (HlONPs) having particle diameter of 14 nm. The XRD (X-ray diffraction) patterns of the obtained hydrophobic FeO nanoparticles (HlONPs) was shown in FIG. 2.

2. Preparation of Hydrophilic FeO Nanoparticles (WIONPs)

Figure 3:
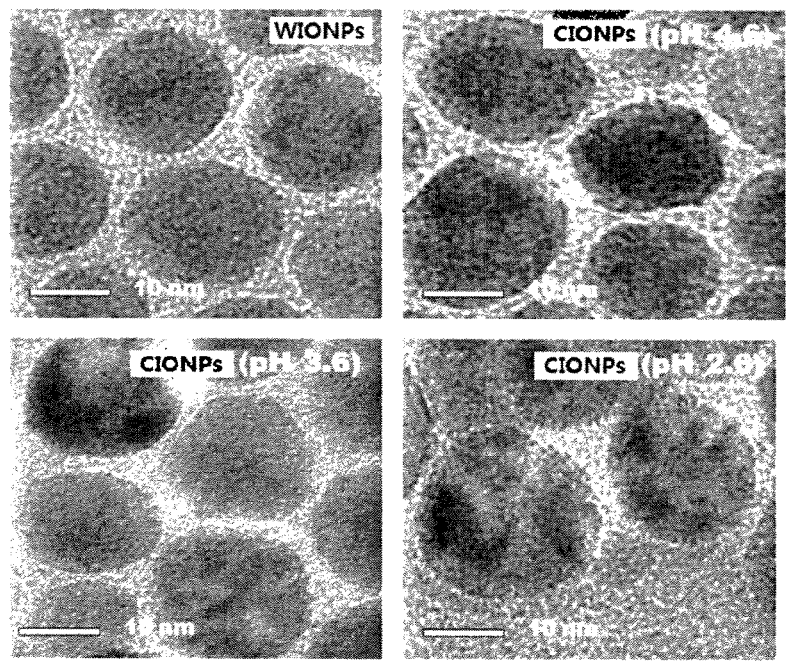
FIG. 3 shows TEM (Transmission electron microscopy) images of "hydrophilic FeO nanoparticles (WIONPs)" and "$Fe_3O_4$ nanoparticles having an interior space (CIONPs)" according to an embodiment of the present invention.
Figure 4:
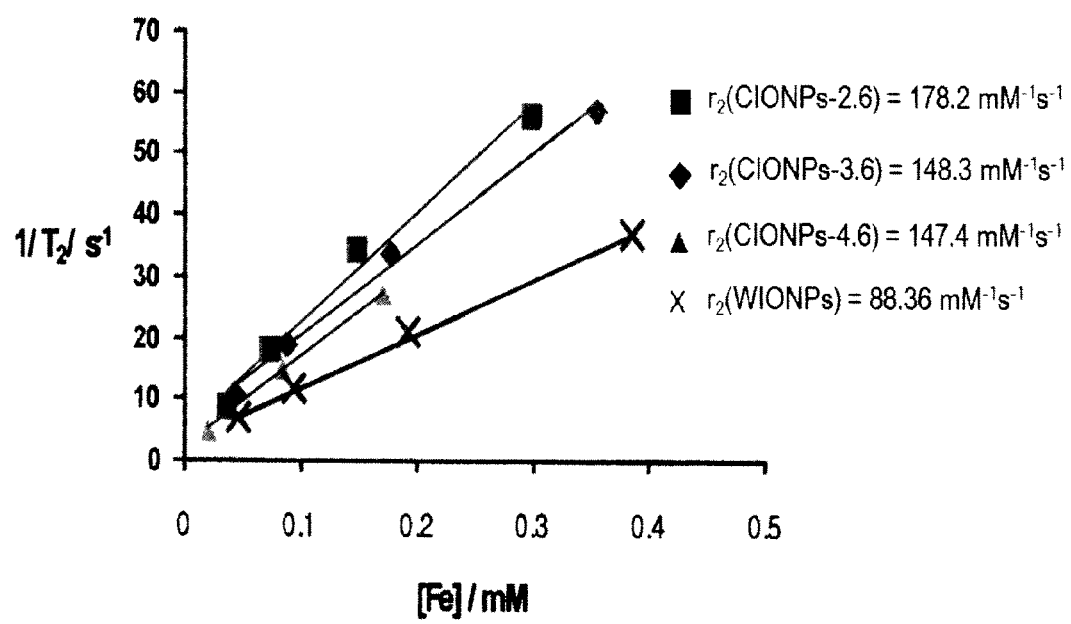
FIG. 4 is a graph showing $r_2$ values and $1/T_2$ values according to Fe concentrations of $Fe_3O_4$ nanoparticles having an interior space (sample, CIONPs at pH=4.6: ▲, CIONPs at pH=3.6: ♦, CIONPs at pH=2.6: ■) prepared by dispersing hydrophilic FeO nanoparticles (WIONPs) in water for 1 day and contacting the nanoparticles to an acidic buffer for 1 day.
Figure 5:
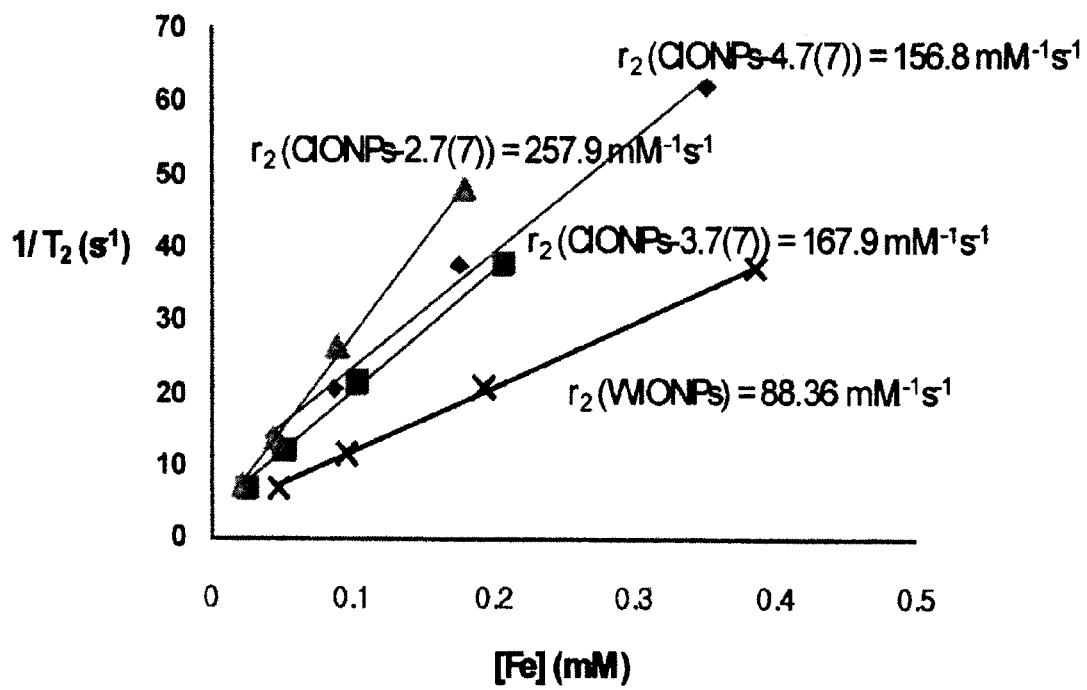
FIG. 5 is a graph showing $r_2$ values and $1/T_2$ values according to Fe concentrations of $Fe_3O_4$ nanoparticles having an interior space (sample, CIONPs at pH=4.7: ♦, CIONPs at pH=3.7: ■, CIONPs at pH=2.7: ▲) prepared by dispersing hydrophilic FeO nanoparticles (WIONPs) in water for 1 day and contacting the nanoparticles to an acidic buffer for 7 days.

30 mg of HlONPs prepared in Step 1 were mixed and dispersed in 10 mL of chloroform (CHCl$_3$). 30 mg of DSPE-mPEG 2000 (1,2-distearoyl-sn-glycero-3-phosphoethanolamine-N-methoxy-polyethylene glycol, polyethylene glycol-phospholipid conjugate) was dissolved in 10 mL of chloroform (CHCl$_3$), and added to the HlONPs solution. After reacting for 1 hour, solvent was slowly removed and the remaining materials were leaved in a vacuum oven of 80° C. for 1 hour. The reactants were cooled to room temperature, dispersed in distilled water, and filtrated with a syringe filter. The size and structure of the synthesized hydrophilic FeO nanoparticles (WIONPs) were measured using TEM (Transmission electron microscopy), and the photograph is shown at the left upper part of FIG. 3(WIONPs). Also, the concentration of Fe was measured with ICP-AES (Inductively coupled plasma atomic emission spectroscopy), and $r_2$ (relaxivity) value and $1/T_2$ value of the hydrophilic FeO nanoparticles (WIONPs) according to the concentration of Fe were measured with MRI (4.7 T). The results are shown in FIG. 4, FIG. 5 and Table 1 (data represented "WIONPs" and marked "X" in graphs and Table 1).

3. Oxidation of Hydrophilic FeO Nanoparticles (WIONPs)

The hydrophilic FeO nanoparticles (WIONPs) prepared in Step 2 were dispersed in water for predetermined periods (1 day), and slowly oxidized to Fe$_3$O$_4$ from their surfaces to the inner part, to produce partially oxidized hydrophilic FeO nanoparticles having oxidized portions of various thicknesses.

4. Preparation of Fe$_3$O$_4$ Nanoparticles Having Interior Space (CIONPs)

Figure 2:
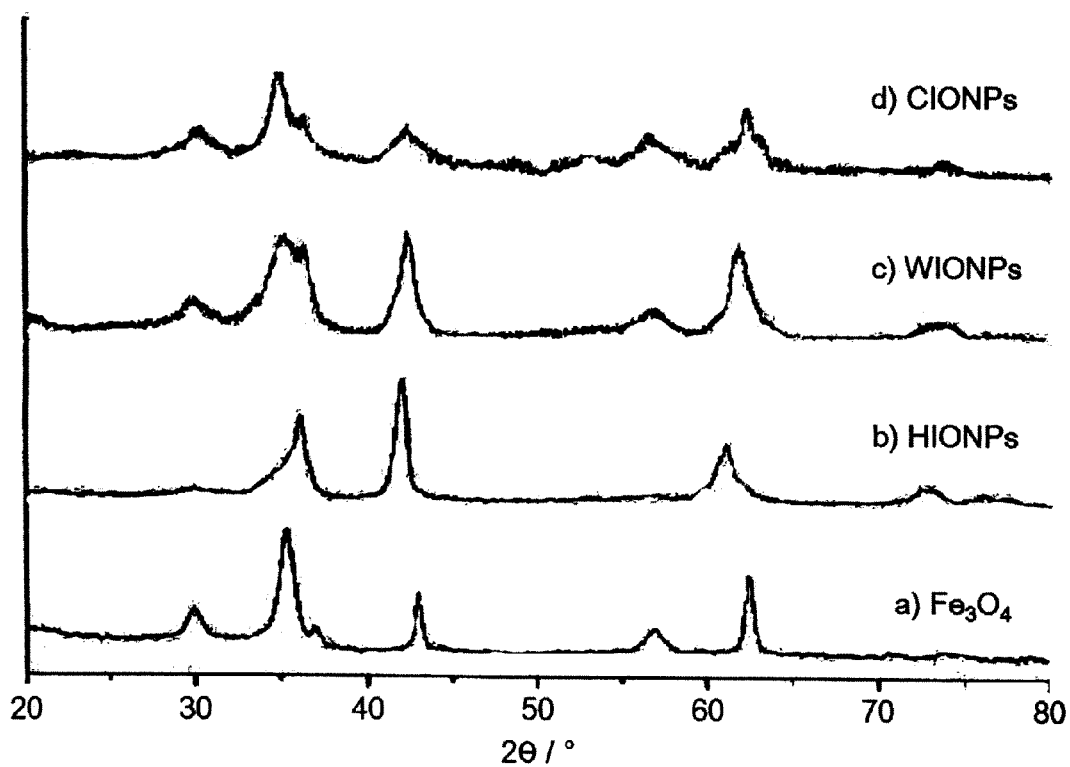
FIG. 2 is a graph for showing XRD (X-ray diffraction) patterns of a) conventional $Fe_3O_4$ nanoparticles, b) hydrophobic FeO nanoparticles (HIONPs), c) hydrophilic FeO nanoparticles (WIONPs) and d) $Fe_3O_4$ nanoparticles having an interior space (CIONPs) according to an embodiment of the present invention.

Each 1 mL of the nanoparticle solution of Step 3 was added to acidic buffers of various concentrations (phthalate buffers of pH=4.6, 3.6 and 2.6), and vortexed for 1 day and 7 days, respectively. After vortexing, the reaction solution was centrifuged to separate nanoparticles, and the separated nanoparticles were washed by centrifugation using distilled water, and dispersed in distilled water, and filtrated with a syringe filter to obtain Fe$_3$O$_4$ nanoparticles having interior space (CIONPs). XRD pattern of the prepared iron oxide (Fe$_3$O$_4$) nanoparticles having interior space is shown in FIG. 2. Also, the size and structure of the prepared nanoparticles were measured with TEM, and the TEM photographs are shown at the right upper part (pH=4.6), the left lower part (pH=3.6), and the right lower part (pH=2.6)) of FIG. 3. Also, the concentrations of Fe was measured with ICP-AES, and $T_2$ values of CIONPs according to the concentrations of Fe were measured with MRI (4.7 T), and $r_2$ (relaxivity) values of CIONPs were calculated. The results are shown in FIG. 4, FIG. 5 and Table 1. FIG. 4 is graphs showing $r_2$ values and $1/T_2$ values according to Fe concentrations of the iron oxide (mostly Fe$_3$O$_4$) nanoparticles having interior space or crack (CIONPs) which were prepared by dispersing hydrophilic iron oxide (FeO) nanoparticles (WIONPs) to water for 1 day and contacting to acidic buffer for 1 day (CIONPs at pH=4.6: ▲, CIONPs at pH=3.6: ♦, CIONPs at pH=2.6: ■). FIG. 5 is graphs showing $r_2$ values and $1/T_2$ values according to Fe concentrations of the iron oxide nanoparticles having interior space (CIONPs) which were prepared by dispersing hydrophilic iron oxide (FeO) nanoparticles (WIONPs) to water for 1 day and contacting to acidic buffer for 7 days (CIONPs at pH=4.7: ♦, CIONPs at pH=3.7: in, CIONPs at pH=2.7: ▲).

TABLE 1

| nanoparticles | contact time in acidic buffer | $T_2$[ms] | $r_2$[s$^{-1}$mM$^{-1}$] |
|---|---|---|---|
| WIONPs | — | 122 | 88.4 |
| CIONPs-4.6 | 1 day | 69 | 147.7 |
| CIONPs-3.6 | 1 day | 65 | 148.3 |
| CIONPs-2.6 | 1 day | 44 | 178.2 |
| CIONPs-4.7(7) | 7 days | 55 | 156.8 |
| CIONPs-3.7(7) | 7 days | 49 | 167.9 |
| CIONPs-2.7(7) | 7 days | 24 | 257.9 |

In Table 1, $T_2$[ms] were measured at the concentration of 0.08 mM(measured with ICP-AES).

As shown in FIG. 4, FIG. 5 and Table 1, the $r_2$ value of the iron oxide (Fe$_3$O$_4$) nanoparticles (CIONPs) of the present invention is larger than the $r_2$ values of the hydrophilic iron oxide (FeO) nanoparticles prepared at Step 2 and conventional Fe$_3$O$_4$ nanoparticles of same size. The $r_2$ value of Feridex (a commercial contrast agent) is 120 s$^{-1}$mM$^{-1}$ in 4.7 T MRI.

Example 2

Preparation of Iron Oxide Nano Contrast Agents

Except for using dimercaptosuccinic acid (DMSA) instead of polyethylene glycol-phospholipid conjugate (PEG-phospholipid) of Step 2, and increasing the reaction time to 12 hours instead of 1 hour of Step 2, iron oxide (mostly Fe$_3$O$_4$) nanoparticles having interior space (CIONPs) was prepared by the same manner as Example 1. The hydrophilic iron oxide (FeO) nanoparticles (WIONPs) of Step 2 were dispersed in water for 1 day, and contacted to acidic buffer (pH=3.6 and 2.6) for 7 days. The concentrations of Fe were measured with ICP-AES, $r_2$ (relaxivity) values of CIONPs were calculated by $T_2$ values of CIONPs according to the concentrations of Fe measured by MRI (4.7 T). The results are shown in Table 2.

TABLE 2

| nanoparticles | contact time in acidic buffer | $T_2$[ms] | $r_2[s^{-1}mM^{-1}]$ |
|---|---|---|---|
| WIONPs | — | 53 | 167.8 |
| CIONPs-3.6(7)[a] | 7 days | 50 | 167.9 |
| CIONPs-3.6(7)[b] | 7 days | 44 | 185.7 |
| CIONPs-2.6(7)[a] | 7 days | 40 | 216.4 |
| CIONPs-2.6(7)[b] | 7 days | 27 | 345.7 |

In Table 2, $T_2$[ms] were measured at the concentration of 0.1 mM(measured by ICP-AES), and "[a]" were CIONPs prepared in Example 1, and "[b]" were CIONPs prepared in Example 2.

As shown in Table 2, the nanoparticles (CIONPs) prepared with dimercaptosuccinic acid as a coating material has larger $r_2$ values and superior contrast effect than the nanoparticles (CIONPs) prepared with polyethylene glycol-phospholipid conjugate as a coating material. Also, the particle size (diameter) of the nanoparticles (CIONPs) prepared with dimercaptosuccinic acid is 48 nm, which is smaller than the particle size (diameter) of the nanoparticles (CIONPs) prepared with polyethylene glycol-phospholipid conjugate (75 nm).

Example 3

Preparation and Test of Iron Oxide ($Fe_3O_4$) Nanoparticle Drug, Carrier

A. Preparation of Iron Oxide ($Fe_3O_4$) Nanoparticle Drug Carrier

An iron oxide (mostly $Fe_3O_4$) nanoparticle drug carrier (DOX-CIONPs) was prepared by mixing an aqueous solution of the iron oxide nano contrast agents ($Fe_3O_4$ nanoparticles having interior space (CIONPs)) prepared in Example 2 and an aqueous solution of anti-cancer medicines (Doxorubicine), and thereby absorbing (loading) the hydrophobic anti-cancer medicines (Doxorubicine) to the interior space of the iron oxide nano contrast agents. The Doxorubicine has a fluorescence property, and thus the loading of the anti-cancer medicines was confirmed by measuring the fluorescence of the DOX-CIONPs.

B. Test of Iron Oxide ($Fe_3O_4$) Nanoparticle Drug Carrier

Figure 6:
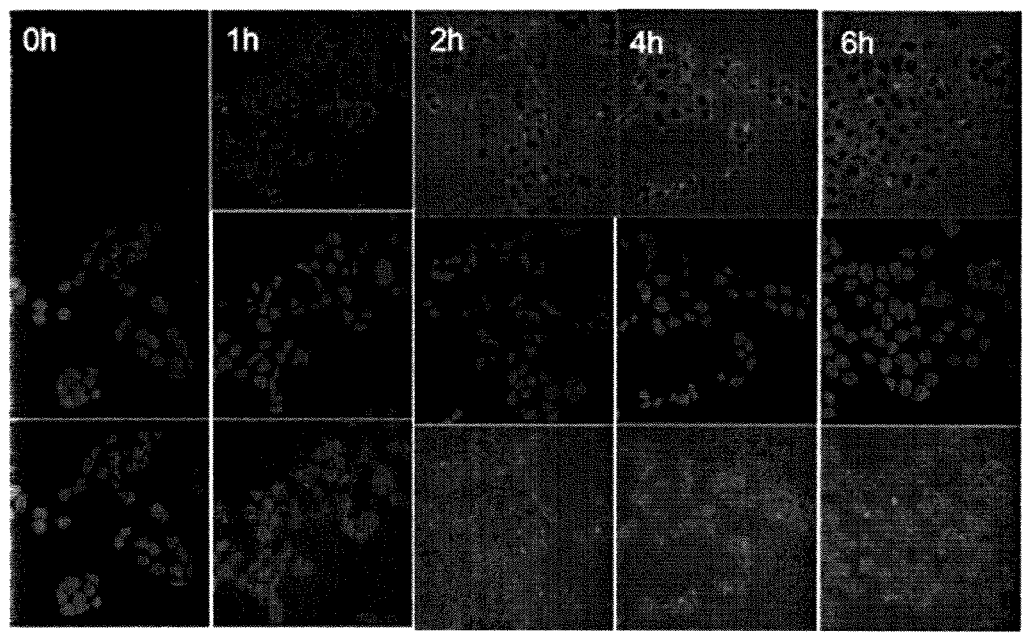
FIG. 6 is fluorescence microscopy images showing the absorption of nanoparticle drug carriers (DOX-CIONPs) into colon cancer (HT-29) cells according to time (0, 2, 4 and 6 hours).

The iron oxide nanoparticle drug carriers (DOX-CIONPs) prepared in Step A were introduced into colon cancer (HT-29) cells, and the degree of absorption according to the incubation time (0, 2, 4, and 6 hours) was measured with a fluorescence microscope. The results are shown in FIG. 6. In FIG. 6, the upper parts show confocal fluorescence microscopy images of DOX-CIONPs, the middle parts show confocal fluorescence microscopy images of cell nucleus of cancer cell dyed with Hoechst33342, and the lower parts show fluorescence microscopy images prepared by adding the upper part images and the middle part images. FIG. 6 shows the absorption of nanoparticle drug carriers (DOX-CIONPs) into colon cancer (HT-29) cells as time passes (0, 2, 4 and 6 hours). As shown in FIG. 6, the dyed positions of cell nucleus are identical to the positions of DOX-CIONPs.

Figure 7:
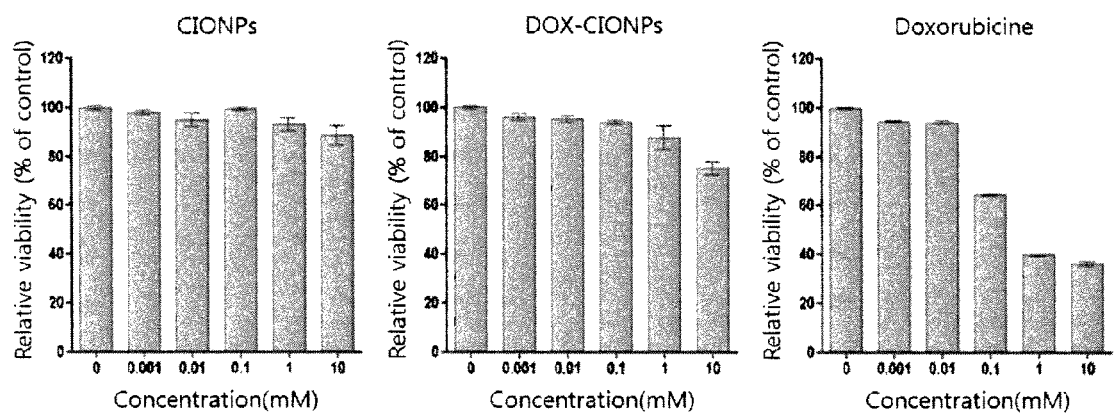
FIG. 7 is graphs showing cell toxicities of iron oxide nano contrast agents (CIONPs), iron oxide ($Fe_3O_4$) nanoparticle drug carriers (DOX-CIONPs) and anti-cancer medicine (Doxorubicine) to colon cancer (HT-29) cells.

Samples were prepared by introducing the nano contrast agents (CIONPs) and the iron oxide ($Fe_3O_4$) nanoparticle drug carriers (DOX-CIONPs) prepared in Examples 2 and 3 and anti-cancer medicines (Doxorubicine) into colon cancer (HT-29) cells by concentrations of 0.001, 0.01, 0.1, 1 and 10 mM. After 24 hours, XTT reagent was added to each sample and relative viability of cancer cells according to the concentration of CIONPs, DOX-CIONPs and anti-cancer medicines (Doxorubicine) were measured. The measurement was carried out by comparing optical absorbances of formazan products from the cancer cells using an absorption spectrometer (XTT assay). The results are shown in FIG. 7. The existence of anti-cancer medicine (Doxorubicine) in the iron oxide ($Fe_3O_4$) nanoparticle drug carriers (DOX-CIONPs) prepared in Step A was confirmed by a toxicity analysis. As shown in FIG. 7, when only the nano contrast agents (CIONPs) of Example 2 was used, the relative viabilities of HT-26 colon cancer cells were over 90% at every concentrations, which means very low toxicity of CIONPs. When only Doxorubicine (anti-cancer medicines) was used, the cancer cells were perished (0.1 mM 35%, 1 mM: 60%, 10 nm 62%) effectively. When DOX-CIONPs of Example 3 was used, the cancer cells were perished (0.1 mM: 6%, 1 mM: 13%, 10 mM: 15%) but less effectively. These results show that DOX-CIONPs are CIONPs containing anti-cancer medicines (Doxorubicine) and can work as a drug carrier.

Figure 8:
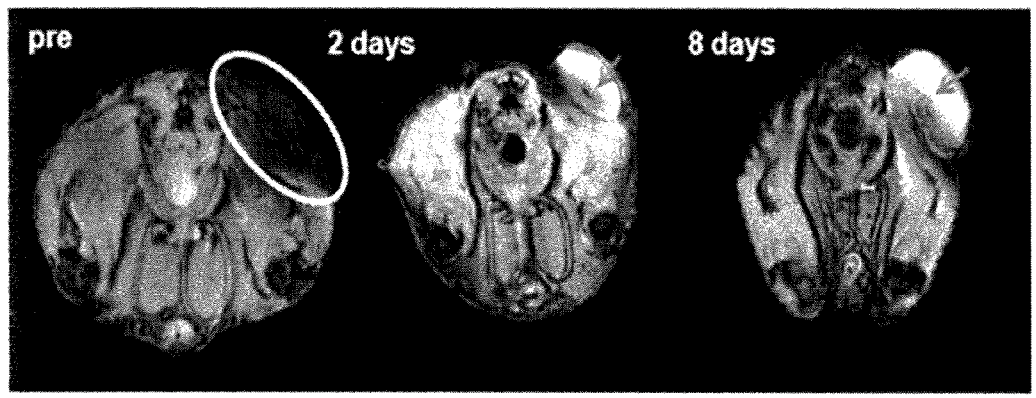
FIG. 8 is MRI $T_2$ weighted contrast images according to time (before injection, 2 days and 8 days after injection) after injecting nanoparticle drug carriers (DOX-CIONPs) to a cancer model which is a nude mouse having colon cancer (HT-29).

A cancer model was prepared by injecting colon cancer (HT-29) to a nude mouse, and the iron oxide ($Fe_3O_4$) nanoparticle drug carrier (DOX-CIONPs) prepared in Step A was injected to the cancer model by intravenous injection (i.v.). The MRI $T_2$ weighted contrast images were obtained as time passes (before the injection, 2 days after and 8 days after the injection), and the results are shown in FIG. 8. As shown in FIG. 8, DOX-CIONPs were diffused and stacked to cancer tissues as time passes. The black parts pointed by the arrows in FIG. 8 represent the diffused and stacked DOX-CIONPs 2 days and 8 days after injection.

From the above results, the iron oxide ($Fe_3O_4$) nanoparticle drug carrier (DOX-CIONPs) according to the present invention has superior contrast effect than a conventional contrast agents, and can be used for a drug delivery.

The invention claimed is:

1. A method for preparing iron oxide nano contrast agents, comprising the steps of:
    coating surfaces of hydrophobic FeO nanoparticles with a coating material selected from the group consisting of polyethylene glycol-phospholipid conjugate, dextran, chitosan, dimercaptosuccinic acid and mixtures thereof in an organic solvent to form hydrophilic FeO nanoparticles having hydrophilic surfaces and dispersibility in water;
    dispersing the hydrophilic FeO nanoparticles in water to oxidize FeO; and
    exposing the oxidized hydrophilic FeO nanoparticles to an acidic buffer solution to dissolve and remove interior unoxidized FeO portions, and thereby to form $Fe_3O_4$ nanoparticles having an interior space,
    wherein the pH of the acidic buffer solution is 2 to 5.

2. The method for preparing iron oxide nano contrast agents of claim 1, wherein the hydrophobic FeO nanoparticles are prepared by oxidizing iron compound selected from the group consisting of Fe(acetylacetonate)$_3$, Fe(NO$_3$)$_3$, Fe(ClO$_4$)$_3$, and mixtures thereof at 250 to 350° C., and have a particle diameter of 5 to 50 nm.

3. The method for preparing iron oxide nano contrast agents of claim 1, wherein the organic solvent, in which the hydrophobic FeO nanoparticles are dispersed, is selected from the group consisting of chloroform (CHCl$_3$), hexane, toluene, dichloromethane and mixtures thereof, and the amount of the organic solvent is 2 to 10 mL with respect to 10 mg of the hydrophobic FeO nanoparticles.

4. The method for preparing iron oxide nano contrast agents of claim 1, wherein, the amount of the coating material is 30 to 200 weight parts with respect to 100 weight parts of the hydrophobic FeO nanoparticles.

5. The method for preparing iron oxide nano contrast agents of claim 1, wherein, in the oxidation step of the hydrophilic FeO nanoparticles, the amount of the water is 5 to 20 mL with respect to 10 mg of the hydrophilic FeO nanoparticles, and the run-time for the oxidation step is 1 to 50 days.

6. The method for preparing iron oxide nano contrast agents of claim 1, wherein, the acidic buffer is selected from the group consisting of phthalate buffer, citrate buffer, acetate buffer and mixtures thereof.

7. The method for preparing iron oxide nano contrast agents of claim 1, wherein the coating material is dimercaptosuccinic acid.

\* \* \* \* \*